United States Patent
Toyota et al.

(10) Patent No.: US 10,555,701 B2
(45) Date of Patent: Feb. 11, 2020

(54) PROBE FOR MEASURING LIP CLOSING FORCE

(71) Applicants: Hiroshima University, Hiroshima (JP); JMS Co., Ltd., Hiroshima (JP)

(72) Inventors: Koichiro Toyota, Hiroshima (JP); Kazuhiro Tsuga, Hiroshima (JP)

(73) Assignees: HIROSHIMA UNIVERSITY, Hiroshima (JP); JMS CO., LTD., Hiroshima (JP)

( * ) Notice: Subject to any disclaimer, the term of this patent is extended or adjusted under 35 U.S.C. 154(b) by 149 days.

(21) Appl. No.: 15/555,577

(22) PCT Filed: Mar. 24, 2016

(86) PCT No.: PCT/JP2016/001710
§ 371 (c)(1),
(2) Date: Sep. 5, 2017

(87) PCT Pub. No.: WO2016/157848
PCT Pub. Date: Oct. 6, 2016

(65) Prior Publication Data
US 2018/0035944 A1    Feb. 8, 2018

(30) Foreign Application Priority Data
Mar. 27, 2015   (JP) .................. 2015-066103

(51) Int. Cl.
*A61B 5/00*   (2006.01)
*A61C 19/05*  (2006.01)
*A61B 5/22*   (2006.01)

(52) U.S. Cl.
CPC .............. *A61B 5/682* (2013.01); *A61B 5/227* (2013.01); *A61B 5/228* (2013.01); *A61B 5/4205* (2013.01);
(Continued)

(58) Field of Classification Search
CPC ....... A61B 5/228; A61B 5/4552; A61B 5/682; A61B 5/70; A61B 2562/0247;
(Continued)

(56) References Cited

U.S. PATENT DOCUMENTS 4,446,747 A    5/1984 Kamm
5,452,727 A  * 9/1995 Tura ...................... A61B 5/224
                                                        128/860
(Continued)

FOREIGN PATENT DOCUMENTS

JP    2001-275994 A    10/2001
JP       3128733 U     1/2007
(Continued)

OTHER PUBLICATIONS

International Search Report for PCT/JP2016/001710 dated Jun. 14, 2016.

Primary Examiner — Catherine B Kuhlman
(74) Attorney, Agent, or Firm — Maschoff Brennan

(57) ABSTRACT

Disclosed herein is a probe 1 for measuring a lip closing force, the probe including: a hollow balloon 10 configured to be disposed between an upper lip 50 and lower lip 51 of a subject, and crushed and deformed by the lip closing force, and a base 20 which is connected to a pressure measurement device 100 for measuring an internal pressure of the balloon 10. The balloon 10 is provided with a fixable portion 13 configured to be sandwiched between teeth 52 and 53 or gums of the subject.

7 Claims, 7 Drawing Sheets

(52) U.S. Cl.
CPC .......... *A61B 5/4542* (2013.01); *A61B 5/4552* (2013.01); *A61B 5/6843* (2013.01); *A61C 19/05* (2013.01); *A61B 2505/09* (2013.01); *A61B 2562/0247* (2013.01); *A61B 2562/164* (2013.01); *A61B 2562/168* (2013.01)

(58) Field of Classification Search
CPC ........ A61B 2562/164; A61B 2562/168; A61B 5/224–228; A61B 2090/064–065; A61C 19/04–05
See application file for complete search history.

(56) References Cited

U.S. PATENT DOCUMENTS

2003/0078521 A1* 4/2003 Robbins ................ A61B 5/228
600/587
2003/0163065 A1 8/2003 Nakao

FOREIGN PATENT DOCUMENTS

| JP | 2008212576 A | 9/2008 |
| JP | 2013135728 A | 7/2013 |
| JP | 2013180189 A | 9/2013 |

\* cited by examiner

PROBE FOR MEASURING LIP CLOSING FORCE

TECHNICAL FIELD

The present invention relates to a probe for measuring a lip closing force.

BACKGROUND ART

It has been known that many organs are associated with a series of movements of a human in masticating and swallowing food taken into his or her mouth (eating and swallowing movements). In particular, teeth, a jaw, cheeks, lips, and a tongue are closely related to mastication of food. If the functions of organs are impaired by, for example, disorders or any other possible causes, what is important is to examine and measure the impaired functions of the organs so as to determine whether the eating and swallowing movements are well performed, or to what degree the movements are done. If rehabilitation of eating and swallowing functions is carried out, it is also important to study the effect of the rehabilitation.

The function of the lips, among the above-listed organs, can be measured by a commonly known method of measuring a force closing upper and lower lips (i.e., a lip closing force). For example, Patent Document 1 discloses a method of measuring the lip closing force. According to this method, a tip end portion of a long and narrow, plate-shaped tool, provided with a pressure sensing part having a pressure sensor, is disposed between the upper and lower lips, and a portion of the tool with the pressure sensing part is sandwiched between the upper and lower lips to measure the lip closing force.

CITATION LIST

Patent Document

Patent Document 1: Japanese Unexamined Patent Publication No. 2013-180189

SUMMARY OF THE INVENTION

Technical Problem

In use of the plate-shaped tool disclosed by Patent Document 1, the tip end portion of the tool is merely disposed between the upper and lower lips. Thus, the tool may become unstable. In particular, if the lip closing force of a subject were lowered by a functional disorder, the tool would be more unstable. Therefore, the tool needs to he stabilized by hand. However, if the tool is held by hand, the pressure sensing part may be pressed onto the upper or lower lip by the force applied by hand. This may cause an error of measurement by the pressure sensing part.

In view of the foregoing background, it is therefore an object of the present invention to measure the lip closing force with high precision and stability.

Solution to the Problem

To achieve the object, according to the present invention, a balloon is used to measure the lip closing three, and the balloon is provided with a portion to be sandwiched between teeth or gums of a subject for fixation of the balloon.

More specifically, the present invention is directed to a probe for measuring a lip closing force. The probe includes: a hollow balloon configured to be disposed between upper and lower lips of a subject, and crushed and deformed by the lip closing; force; and a base which communicates with the inside of the balloon, and is connected to a pressure measurement device for measuring an internal pressure of the balloon, wherein the balloon is provided with a fixable portion configured to be sandwiched between teeth or gums of the subject.

According to this configuration, with the balloon disposed between the upper and lower lips of the subject, the fixable portion of the balloon is sandwiched between the teeth or gums of the subject to fix the fixable portion. Thus, the balloon is positioned. When the subject applies a three closing the lips to the balloon in this state, the balloon is crushed, thereby increasing the internal pressure of the balloon. The pressure is measured by the pressure measurement device, based on which the magnitude of the lip closing force is obtained. During the measurement of the lip closing force, the possibility of misalignment of the balloon is reduced. This may substantially prevent the balloon from slipping between the upper and lower lips, and being misaligned, and thus, the lip closing force may be measured with high precision.

The fixable portion may have the shape of a plate extending from a portion of the balloon on a back side in a direction of insertion of the balloon between the lips.

According to this configuration, with the balloon disposed between the upper and lower lips, the fixable portion is naturally inserted into the oral cavity, and may be easily sandwiched between the teeth or the gums.

The fixable portion may extend to a position corresponding to front teeth in an oral cavity of the subject so as to be sandwiched between the front teeth or gums of the subject.

According to this configuration, for example, even a subject who has no back teeth and cannot sandwich an object between the back teeth may sandwich the fixable portion between his or her front teeth. Thus, the possibility of misalignment of the balloon may be reduced. Further, when a subject having complete dentures does not wear them, the fixable portion may be sandwiched between his or her front gums. Thus, the possibility of misalignment of the balloon may be reduced.

The fixable portion may be provided with a protrusion protruding in a vertical direction.

According to this configuration, when the fixable portion is sandwiched between the teeth or the gums, the protrusion is hooked on the teeth or the gums. Thus, the fixable portion does not easily come out of a space between the teeth or the gums. As a result, the balloon is further stabilized.

The fixable portion may extend to a position corresponding to back teeth in an oral cavity of the subject so as to be sandwiched between the back teeth or gums of the subject.

According to this configuration, even a subject who cannot sandwich an object between his or her from teeth may sandwich the fixable portion between his or her back teeth. Thus, the possibility of misalignment of the balloon may be reduced. Further, when a subject having complete dentures does not wear them, the fixable portion may be sandwiched between his or her back gums. Thus, the possibility of misalignment of the balloon may be reduced.

The fixable portion may include a right extension extending rightward, and a left extension extending leftward, in the oral cavity of the subject.

According to this configuration, the left and right extensions of the fixable portion are respectively disposed in the left and right regions of the oral cavity of the subject. Thus, the subject may sandwich the left and right extensions between his or her back teeth or gums. Thus, the balloon is further stabilized.

The fixable portion may be integrally molded within the balloon.

According to this configuration, the number of components of the probe for measuring the lip closing force may be reduced, and the probe may be provided at low cost.

Advantages of the Invention

The balloon configured to be disposed between the upper and lower lips of the subject is provided with the fixable portion configured to be sandwiched between the teeth or gums of the subject. This may reduce the possibility of misalignment of the balloon during the measurement of the lip closing force. Thus, the lip closing force may be measured with high precision and stability.

Further, if the fixable portion extends from the back portion of the balloon in the direction of the insertion of the balloon, the fixable portion may be easily sandwiched between the teeth or the gums.

Moreover, if the fixable portion is configured to be sandwiched between the front teeth or front gums of the subject, the lip closing force of a subject who cannot sandwich an object between his or her back teeth may be measured with high precision and stability.

If the fixable portion is provided with the protrusion protruding in the vertical direction, the fixable portion does not easily come out of a space between the teeth or the gums a result, the balloon is further stabilized.

In addition, if the fixable portion is configured to be sandwiched between the back teeth or back gums of the subject, the lip closing force of a subject who cannot sandwich an object between his or her front teeth may be measured with high precision and stability.

Furthermore, if the fixable portion has the left and right extensions configured to be sandwiched between the back teeth or gums, the balloon is further stabilized.

On top of that, if the fixable portion is integrally molded with the balloon, the number of components may be reduced, and the probe may be provided at low cost.

DESCRIPTION OF EMBODIMENTS

Embodiments of the present invention will now be described in detail with reference to the drawings. Note that the following description of embodiments is merely an example in nature, and is not intended to limit the scope, application, or uses of the present invention.

First Embodiment

Figure 1:
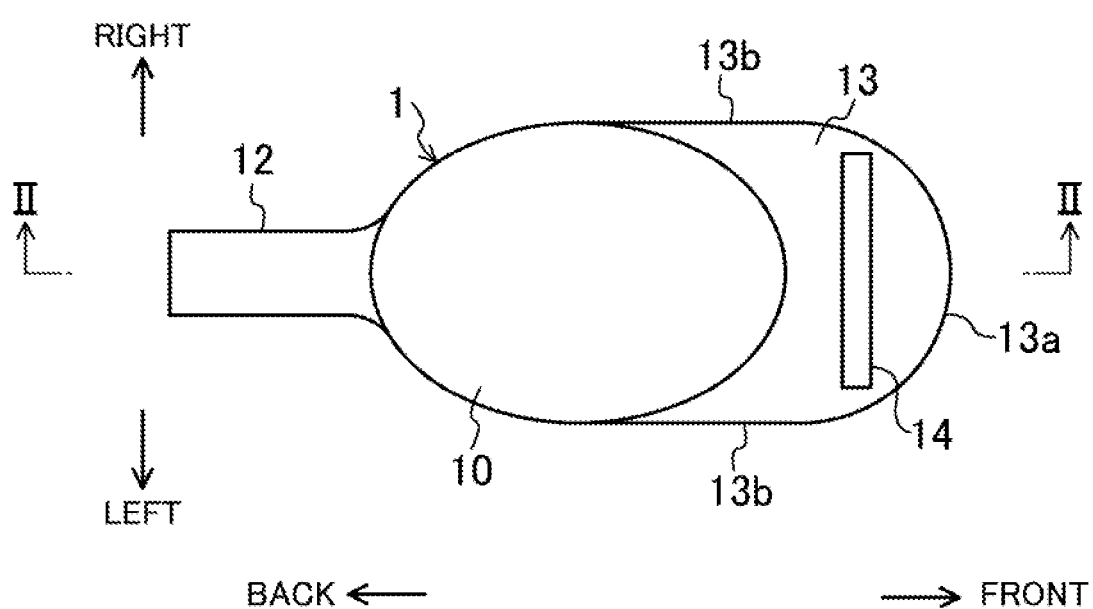
FIG. 1 is a plan view illustrating a balloon of a probe for measuring a lip closing force according to a first embodiment.
Figure 4:
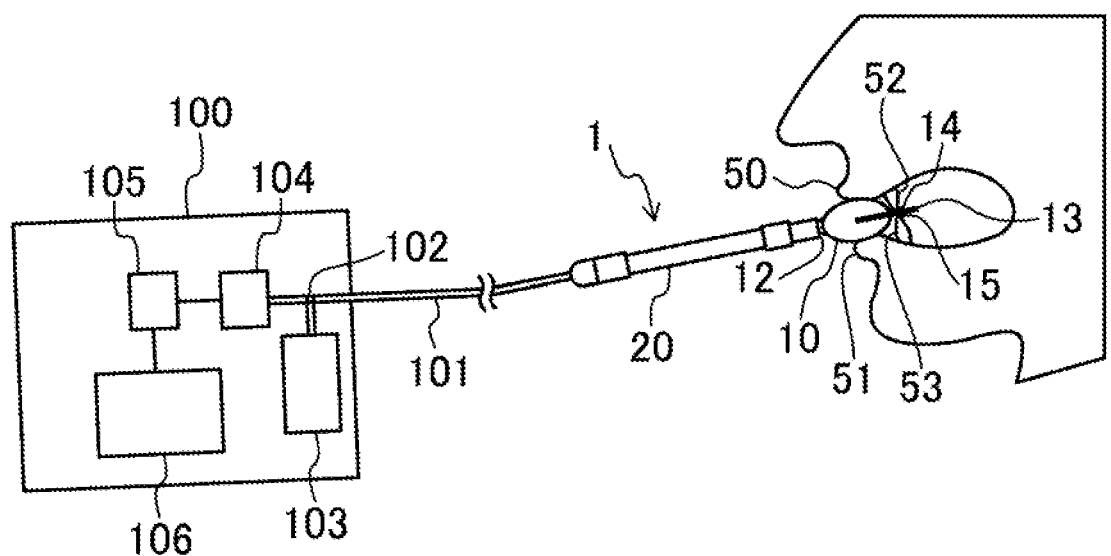
FIG. 4 is a view illustrating a state where the balloon of the probe for measuring the lip closing force is disposed between upper and lower lips of a subject.
Figure 5:
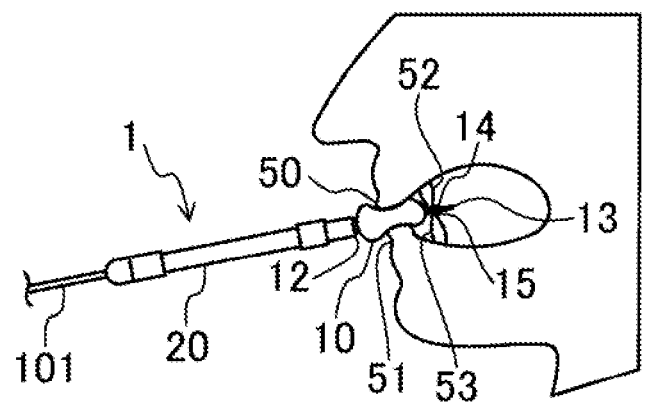
FIG. 5 is a view illustrating how a lip closing force is measured.

FIG. 1 is a plan view illustrating an enlargement of a balloon 10 of a probe 1 for measuring a lip closing force shown in FIG. 4. The probe 1 for measuring the lip closing force according to the first embodiment is used to measure a force closing; upper and lower lips, i.e., a lip closing force. As shown in FIG. 4, the probe 1 for measuring the lip closing force includes: a hollow balloon 10 which is disposed between the upper and lower lips of a subject, and crushed and deformed by the lip closing force; and a base 20 which communicates with the inside of the balloon 10, and is connected to a pressure measurement device 100 for measuring an internal pressure of the balloon 10.

In the following description of the embodiments, with reference to a direction of insertion of the balloon 10 between the lips, a side closer to the back of an oral cavity will be referred to as a "back" side, and another side away from the back of the oral cavity will be referred to as a "front" side. Further, with the balloon 10 inserted between the lips, a left side of the balloon as seen from the subject will be simply referred to as the "left," and a right side of the balloon as seen from the subject will be simply referred to as the "right."

First, a pressure measurement device 100 will be described with reference to FIG. 4. The pressure measurement device 100 may be a generally known device. For example, a device disclosed by Japanese Unexamined Patent Publication No. 2001-275994 may be used. Specifically, the pressure measurement device 100 includes a tube 101, a valve 102, a pressurizing unit 103, a pressure sensor 104, a data processing unit 105, and a display unit 106. The tube 101 is a thin, soft tube. A tip end of the tube 101 communicates with the inside of the balloon 10 via the base 20. A base end of the tube 101 is hermetically connected to the pressure sensor 104. The pressure sensor 104 may be a generally known piezoelectric element, for example. The valve 102 is provided at some midpoint of the tube 101. The pressurizing unit 103 is connected to a branch of the tube 101 extending from the junction between the tube 101 and the valve 102. The pressurizing unit 103 is comprised of a pump which pumps the air into the balloon 10 until the internal pressure of the balloon. 10 reaches a predetermined pressure. The valve 102 is configured to be switchable between a state where a portion of the tube 101 closer to the balloon 10 than the valve 102 communicates with the pressurizing unit 103, and a state where the same portion does not communicate with the pressurizing unit 103.

The data processing unit 105 is configured to process an electric signal received from the pressure sensor 104 to convert the signal into a pressure value. The display unit 106 may be, for example, a display panel which shows the pressure value in a visually recognizable manner.

Figure 2:
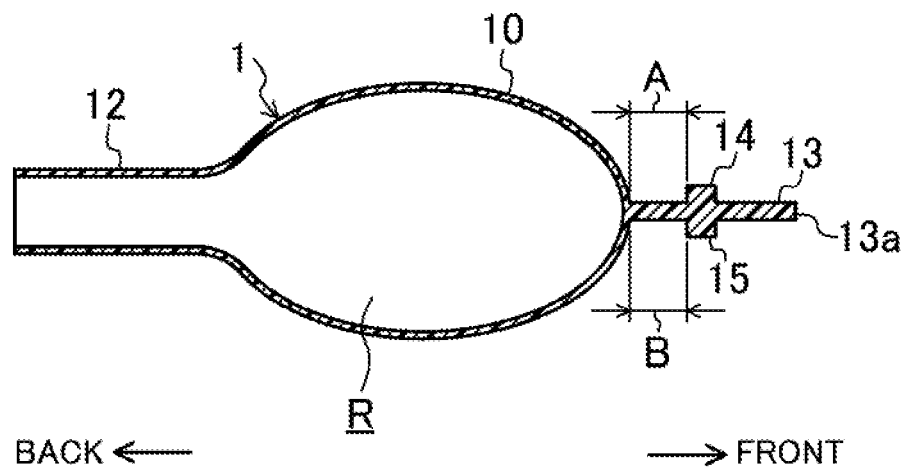
FIG. 2 is a cross-sectional view taken along a plane of FIG. 1.

The balloon 10 may be entirely made of an elastic body such as natural rubber, synthetic rubber, or silicone rubber, and is configured as a member having a hollow portion R as shown in FIG. 2. The balloon 10 is easily crushed and deformed when the lip closing force is exerted as an external force on the balloon 10, and returns to the original shape when the external force no longer exists. As shown in FIG. 1, the balloon 10 has a dimension in the direction of insertion between the lips larger than a dimension in a transverse direction, i.e., the balloon 10 is oblong. Further, the balloon 10 has a thickness (a dimension in the vertical direction) smaller than the transverse dimension.

A back portion of the balloon 10 is constituted of a curved surface which is curved such that its center in the transverse direction is the closest to the back of the oral cavity. A front portion of the balloon 10 is constituted of a curved surface which is curved such that its center in the transverse direction is the farthest from the back of the oral cavity. Thus, the transverse dimension of the balloon it) is maximum at the center in the insertion direction, and gradually decreases toward the back and front portions. Further, the balloon 10 has a lower surface which bulges downward such that its center is located at the lowermost position. The balloon 10 has an upper surface which bulges upward such that its center is located at the uppermost position. Thus, when viewed from the side, the balloon 10 has a thickness gradually decreasing from the center toward the back and front portions.

A pipe 12 which communicates with the inside of the balloon 10 is integrally molded with the front portion of the balloon 10. The pipe 1 protrudes forward from the transverse center of the front portion of the balloon 10. The base 20 shown in FIG. 4 is connected to the pipe 12. The base 20 may be comprised of a molded tubular member made of a hard resin, for example. The base 20 is so hard as not to be crushed or deformed even when the base 20 is bitten by the subject. An end of the base 20 opposite to the balloon 10 is connected to the pressure measurement device 100 via the tube 101. Thus, a change in internal pressure of the balloon 10 is transmitted to the pressure sensor 104 via the base 20 and the tube 101.

The balloon 10 has a fixable portion 13 which is integrally molded with the back portion of the balloon 10. Integrally molding the fixable portion 13 with the balloon 10 reduces the number of components. Thus, the balloon 10 may be provided at low cost. As shown in FIG. 4, the fixable portion 13 may be as thick as, or thicker than, the balloon 10. The fixable portion 13 extends to a position corresponding to upper front teeth 52 and lower front teeth 53 in the oral cavity of the subject, and is vertically sandwiched and fixed between the upper and lower front teeth 52 and 53. Note that when a subject having complete dentures does not wear them, for example, the fixable portion 13 may be vertically sandwiched between his or her front gums.

As shown in FIG. 1, the fixable portion 13 extends in the transverse direction. The fixable portion 13 has a back edge 13a, of which a center portion in the transverse direction is located closest to the back of the oral cavity. Left and Right edges 13b, 13b of the fixable portion 13 extend linearly from left and right side surfaces of the balloon 10 toward the back, and are connected to the back edge 13a of the fixable portion 13. The left and right, edges 13b, 13b of the fixable portion 13 are substantially parallel to each other. Further, the fixable portion 13 has a transverse dimension which is substantially the same as the maximum transverse dimension of the balloon 10.

Figure 3:
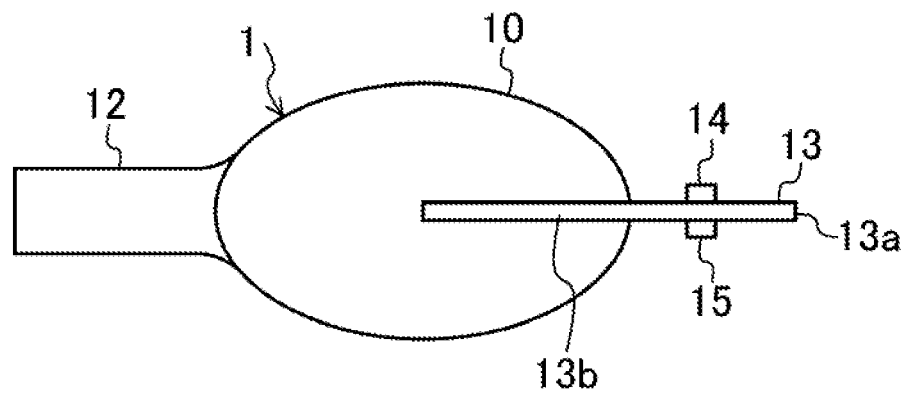
FIG. 3 is a left side view of the balloon.

As shown in FIGS. 2 and 3, an upper surface of the fixable portion 13 is provided with an tipper protrusion 14 protruding upward and extending in the transverse direction. The upper protrusion 14 is located between the back edge of the fixable portion 13 and the back edge of the balloon 10 to be spaced rearward from the back edge of the balloon 10, such that the upper front teeth 52 can rest between the upper protrusion 14 and the back edge of the balloon 10. That is, as shown in FIG. 2, a distance A between the upper protrusion 14 and the back edge of the balloon it) is set to allow the upper front teeth 52 to fit between the upper protrusion 14 and the back edge of the balloon 10. As shown in FIG. 1, the upper protrusion 14 has a smaller transverse dimension than the fixable portion 13. The upper protrusion 14 is substantially rectangular when viewed in section.

Further, the fixable portion 13 has a lower surface provided with a lower protrusion 15 protruding downward and extending in the transverse direction. The lower protrusion 15 is arranged in the same manner as the upper protrusion 14, such that a distance B between the lower protrusion 15 and the back edge of the balloon 10 is set to allow the lower front teeth 53 to fit between the lower protrusion 15 and the back edge of the balloon 10. Both or one of the upper and lower protrusions 14 and 15 may be omitted.

In this embodiment, the upper and lower protrusions 14 and 15 are arranged to overlap with each other in the vertical direction when viewed in plan. However, this arrangement is not limiting, and the upper protrusion 14 may be arranged forward of the lower protrusion 15. Further, in this embodiment, the upper and lower protrusions 14 and 15 extend linearly in the transverse direction. However, this arrangement is not limiting, and the upper and lower protrusions 14 and 15 may be bent with their transverse center portions located farthest from the back of the oral cavity so as to extend along the rows of the front teeth 52 and 53.

How the probe 1 configured as described above is used for the measurement of the lip closing force will be described below. First, the base 20 of the probe 1 for measuring the lip closing force is connected to the tube 101. Then, the valve 102 is operated to allow a portion of the tube 101 closer to the balloon 10 than the valve 102 to communicate with the pressurizing unit 103. Then, the pressurizing unit 103 is operated to send the air into the balloon 10 until the internal pressure of the balloon 10 reaches a predetermined pressure. The pressure sensor 104 can determine whether the internal pressure has reached the predetermined pressure or not. When the internal pressure of the balloon 10 has reached the predetermined pressure, the pressurizing unit 103 is stopped, and the valve 102 is operated to switch to a state where the portion of the tube 101 closer to the balloon 10 does not communicate with the pressurizing unit 103.

Then, the balloon 10 of the probe 1 for measuring the lip closing force is inserted between upper and lower lips 50 and 51 of the subject. The balloon 10 is disposed such that the thickest portion of the balloon 10 comes into contact with the upper and lower lips 50 and 51. The balloon 10 has the fixable portion 13 extending toward the back. Thus, the fixable portion 13 is located further backward than a position corresponding to the front teeth 52 and 53 in the oral cavity. When the balloon 10 is inserted between the upper and lower lips 50 and 51 and the fixable portion 13 is vertically sandwiched between the front teeth 52 and 53, the fixable portion 13 is fixed. At this time, the upper front teeth 52 rest between the upper protrusion 14 and the balloon 10, and the lower front teeth 52 rest between the lower protrusion 15 and the balloon 10. Thus, the upper front teeth 52 are hooked on the upper protrusion 14, and the lower front teeth 53 are hooked on the lower protrusion 15. This may prevent the fixable portion 13 from moving forward.

Thereafter, the subject applies a force to the balloon 10 so as to vertically sandwich the balloon 10 between the upper and lower lips 50 and 51. This three is the lip closing force. The balloon 10 that has received the lip closing force is crushed and deformed, thereby increasing the internal pressure of the balloon 10. The internal pressure of the balloon 10 is detected by the pressure sensor 104 of the pressure measurement device 100, processed by the data processing unit 105, and then shown on the display unit 106. The display unit 106 may show the internal pressure by a numeric indication, or a relative indication using deep and light colors, for example.

When the lip closing force is applied to the balloon 10, a force that pushes the balloon 10 out of the oral cavity may also be exerted. Even in such a case, since the subject is sandwiching the fixable portion 13 between his or her front teeth 52 and 53, the balloon 10 is less likely misaligned, and may be prevented from slipping between the upper and lower lips 50 and 51. Thus, the lip closing three may be reliably exerted on the balloon 10, and measured h high precision.

Since the lip closing force is measured with high precision, the function of the lips can be examined based on the measurement results. In particular, if rehabilitation of eating and swallowing functions is carried out, the effect of the rehabilitation may be studied with high precision.

Also in the case where the subject sandwiches the fixable portion 13 between his or her front gums, the misalignment of the balloon 10 may be reduced. Thus, the measurement may be conducted with high precision. When sandwiching the fixable portion 13 between his or her front gums, the subject does not significantly feel pain in the gums because the fixable portion 13 is made of an elastic material. Thus, the fixable portion 13 may be firmly sandwiched.

As can be seen, the probe 1 for measuring the lip closing force according to the first embodiment has the balloon 10 configured to be disposed between the upper and lower lips 50 and 51 of the subject, and the balloon 10 is provided with the fixable portion 13 configured to be sandwiched between the front teeth 52, 53 or gums of the subject. This may reduce the possibility of misalignment of the balloon 10 during the measurement of the lip closing force. Thus, the lip closing force may be measured with high precision and stability.

Figure 6:
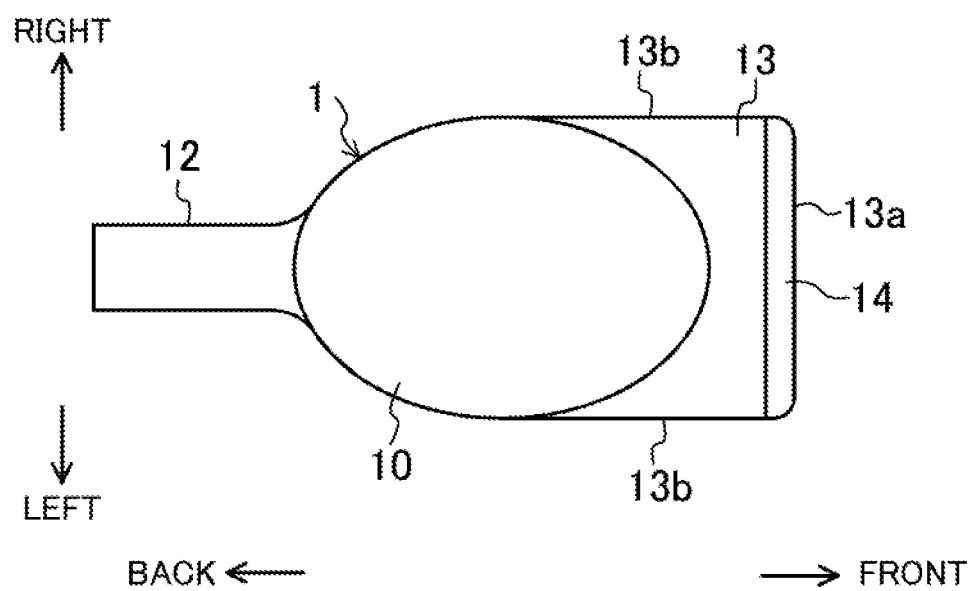
FIG. 6 is a view corresponding to FIG. 1, illustrating an alternative example of the first embodiment.
Figure 7:
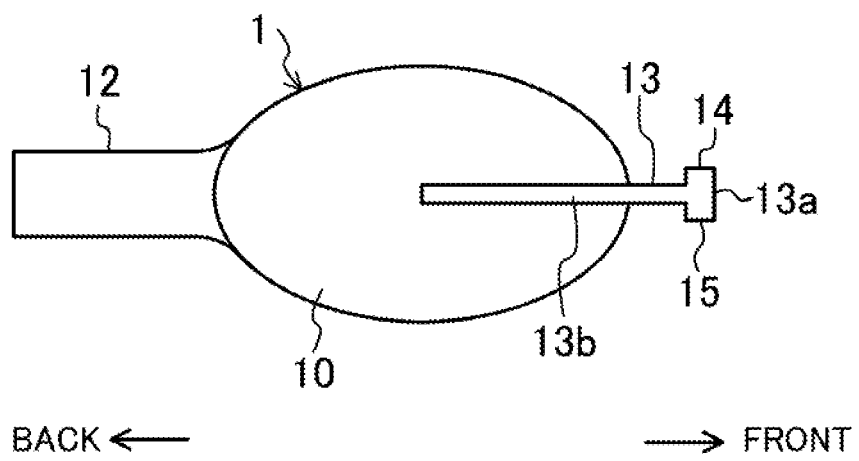
FIG. 7 is a view corresponding to FIG. 3, illustrating an alternative example of the first embodiment.

According to an alternative example of the first embodiment shown in FIGS. 6 and 7, the back edge 13a of the fixable portion 13 may extend linearly in the transverse direction, in this alternative example, the back edge 13a of the fixable portion 13 overlaps with the upper and lower protrusions 14 and 15 when viewed in plan. This arrangement avoids the fixable portion 13 from reaching the back of the cavity, thereby improving usability.

Second Embodiment

Figure 8:
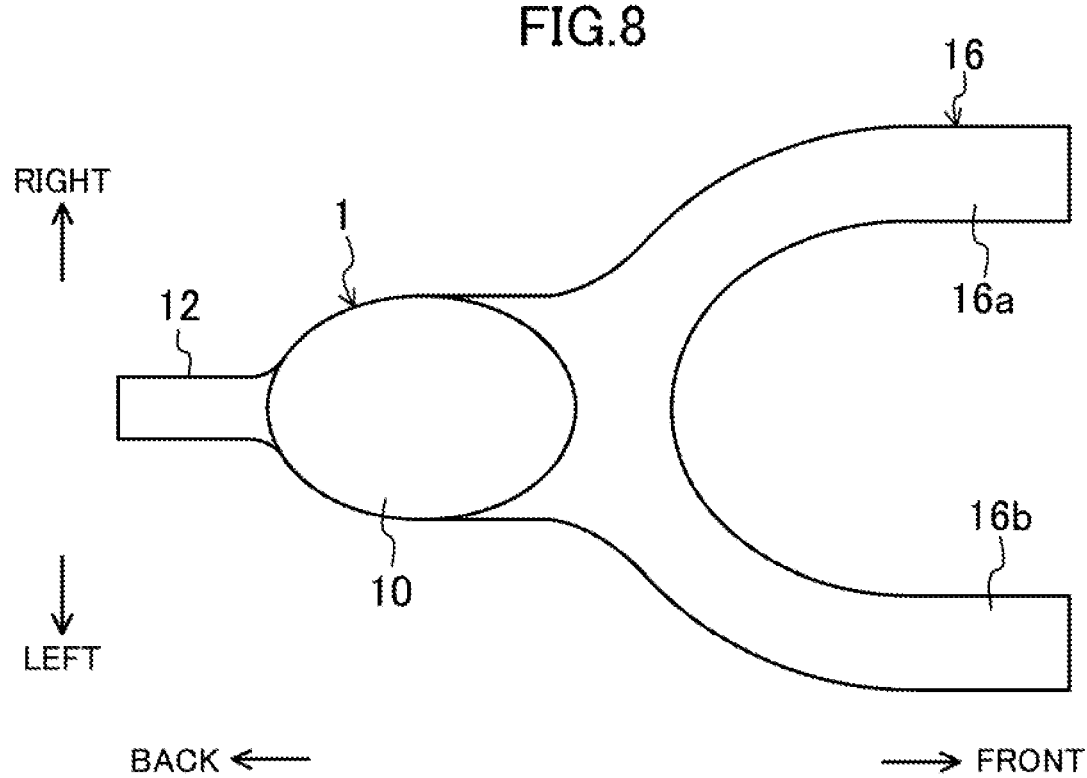
FIG. 8 is a view corresponding to FIG. 1, illustrating a second embodiment.
Figure 9:
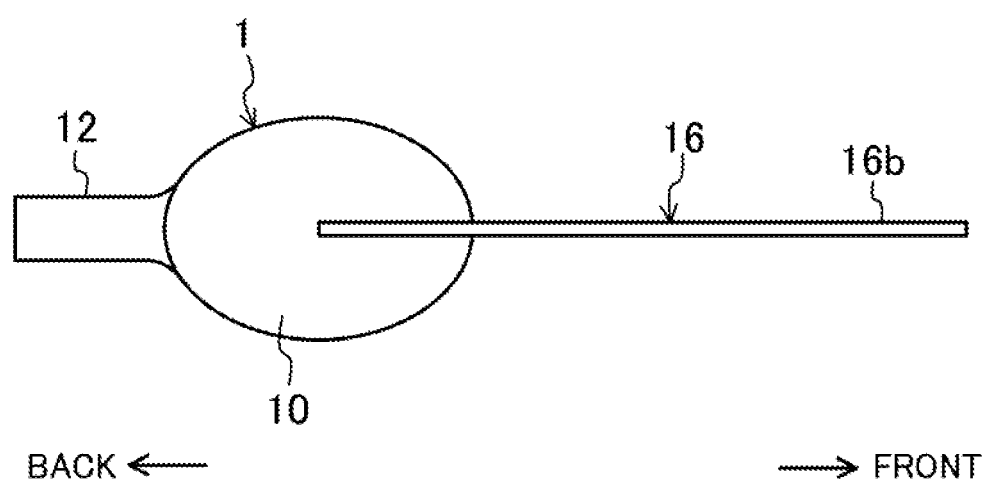
FIG. 9 is a view corresponding to FIG. 3, illustrating the second embodiment.

FIGS. 8 and 9 illustrate a balloon 10 of a probe 1 for measuring a lip closing force according to a second embodiment of the present invention. In the second embodiment, a fixable portion 16 is different from that of the first embodiment in that the fixable portion 16 is configured to be vertically sandwiched between back teeth 54 and 55 (shown in FIGS. 10 and 11) or back gums of a subject. In the second embodiment, components that have been described in the first embodiment are designated by the same reference characters, and are not described in detail. The following description will focus on only differences from the first embodiment.

The fixable portion 16 extends from the back portion of the balloon 10 to a position corresponding to the back teeth 54 and 55 in the oral cavity of the subject, and has the shape of a plate so as to be sandwiched between the back teeth 54 and 55 or the gums. The fixable portion 16 includes a right extension 16a extending rightward, and a left extension 16b extending leftward, in the oral cavity of the subject. When viewed in plan, the right extension 16a is curved such that the more backward it extends, the more rightward it is positioned. Further, when viewed in plan, the left extension 16b is curved such that the more backward it extends, the more leftward it is positioned. Back portions of the right and left extensions 16a and 16b extend substantially linearly. That is, the right and left extensions 16a and 16b extend along the rows of the teeth of the subject.

Figure 10:
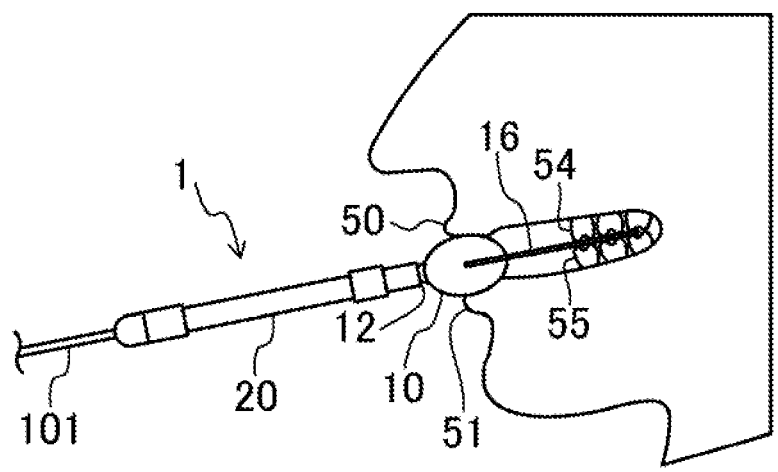
FIG. 10 is a view corresponding to FIG. 4, illustrating the second embodiment.
Figure 11:
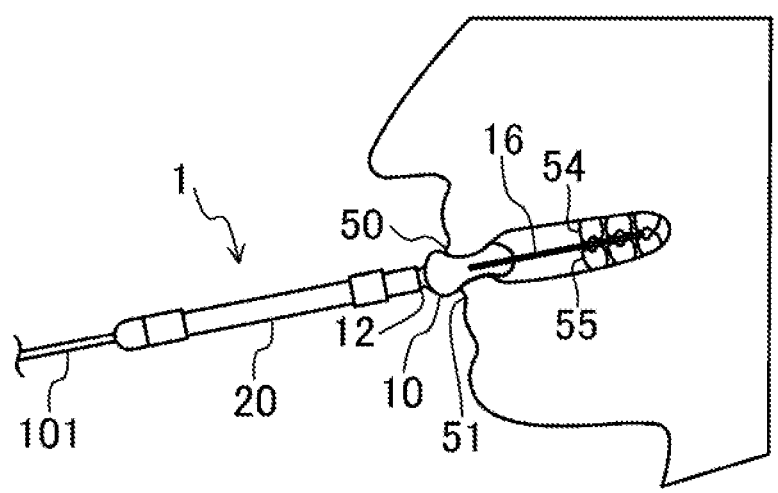
FIG. 11 is a view corresponding to FIG. 5, illustrating the second embodiment.

In use of the balloon 10 of the second embodiment, the fixable portion 16 is inserted deep into the oral cavity until it reaches the back teeth 54 and 55 as shown in FIG. 10. Thus, the fixable portion. 1.6 is vertically sandwiched between the back teeth 54 and 55, which may reduce the possibility of misalignment of the balloon 10. Therefore, just like in the first embodiment, the lip closing force may be measured with high precision and stability.

According to the second embodiment, a subject who cannot sandwich an object between the front teeth may sandwich the fixable portion 16 between his or her back teeth 54 and 55. Thus, the possibility of misalignment of the balloon 10 may be reduced. Further, when a subject having complete dentures does not wear them, the fixable portion 16 may be vertically sandwiched between his or her hack gums. Thus, the possibility of misalignment of the balloon 10 may be reduced.

Note that the fixable portion 16 of the balloon 10 according to the second embodiment may be vertically sandwiched between the front teeth, or both of the front teeth and the back teeth 54 and 55.

Third Embodiment

Figure 12:
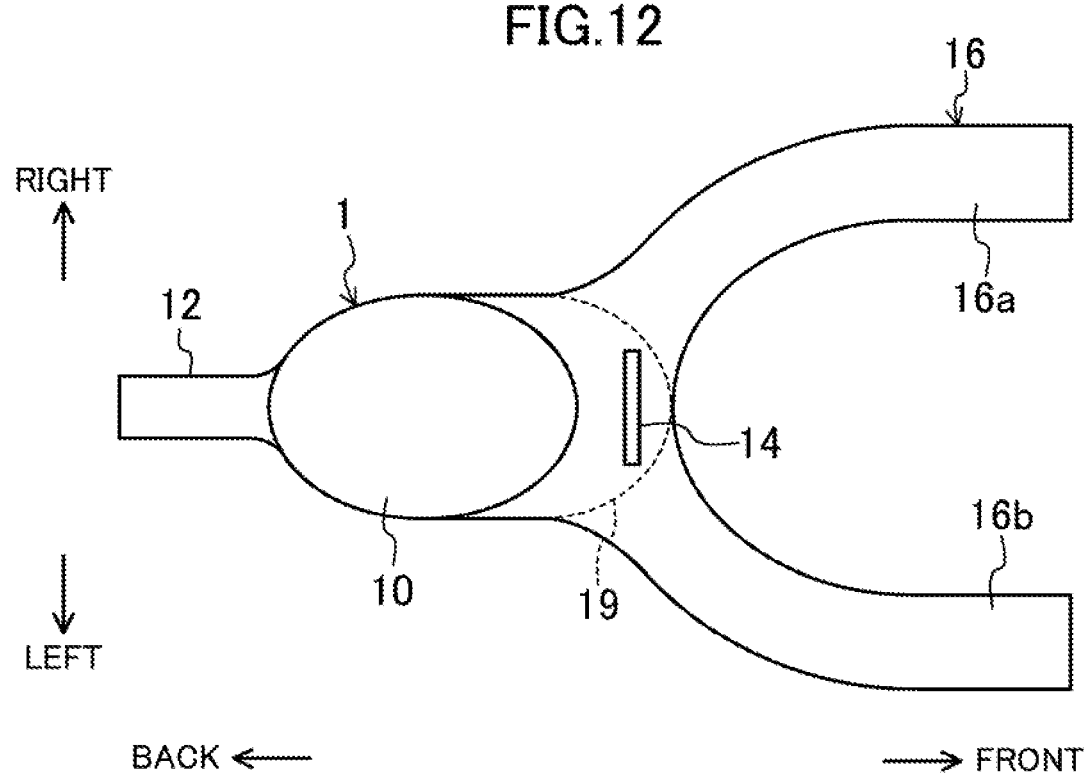
FIG. 12 is a view corresponding to FIG. 8, illustrating a third embodiment.

FIG. 12 illustrates a balloon 10 of a probe 1 for measuring a lip closing force according to a third embodiment of the present invention. In the third embodiment, a fixable portion 16 is different from that of the second embodiment in that a tear-oil portion 19 is provided. In the third embodiment, components that have been described in the second embodiment are designated by the same reference characters, and are not described in detail. The following description will focus on only differences from the second embodiment.

Specifically, the tear-off portion 19 may be, for example, perforation. The tear-off portion 19 extends along the peripheral edge of the fixable portion 13 according to the first embodiment shown in FIG. 1. The fixable portion 16 is provided with the upper protrusion 14 and the lower protrusion (not shown) according to the first embodiment. However, these protrusions may be omitted.

The balloon 10 of the third embodiment may be used without separating the fixable portion along the tear-off portion 19, just like in the second embodiment. Alternatively, the right and left extensions 16a and 16b may be separated along the tear-off portion 19 so that the fixable portion 16 has the same shape as that of the first embodiment, and is sandwiched between the front teeth of the subject. The tear-off portion 19 is not limited to have the shape shown in the drawing, but may have any shape as long as the fixable portion 16 can be sandwiched between the front teeth. The tear-off portion 19 may be, for example, one or more grooves, one or more holes, or one or more thinned regions provided for the fixable portion 16. Alternatively, the tear-off portion 19 may be a fragile region which is weaker than the other regions. The tear-off portion 19 may be weak enough to be torn when a tension is applied thereto by fingers, for example.

According to the first to third embodiments described above, the probe 1 for measuring the lip closing force is connected to the pressure measurement device 100 via the tube 101. However, this configuration is not limiting, and the probe 1 may be directly connected to the pressure measurement device 100.

Further, according to the first to third embodiments described above, the probe 1 for measuring the lip closing force is used only for the measurement of the lip closing force. However, the probe 1 may also be used w measure, for example, a tongue pressure. For the measurement of the tongue pressure, the probe of the first embodiment, which has the relatively short fixable portion 13, is inserted into the oral cavity until the balloon 10 comes onto the tongue. Then, the tongue is lifted upward to crush the balloon 10. In this way, the tongue pressure may be measured. The probe of the second embodiment has the long fixable portion 16. Thus, the fixable portion 16 is entirely or partially cut, and then the probe is inserted into the oral cavity until the balloon 10 comes onto the tongue. Likewise, other pressures related to the oral cavity, such as a sublingual muscle pressure, a lip pressure, and a cheek pressure, may also be measured. For measuring the tongue pressure, the pipe 12 of the balloon 10 may be suitably covered with a hard member. Biting the hard member with the teeth may reduce the possibility of misalignment of the balloon 10.

The embodiments described above are mere examples, and are not to be construed as limiting the scope of the present disclosure. Variations and modifications of equivalents of the claims are all intended to fall within the scope of the present disclosure.

INDUSTRIAL APPLICABILITY

As can be seen in the foregoing, the probe for measuring a lip closing force according to the present invention may be used to measure a force closing lips.

DESCRIPTION OF REFERENCE CHARACTERS

1 Probe for Measuring Lip Closing Force
10 Balloon
13 Fixable Portion
16 Fixable Portion
16*a* Right Extension
16*b* Left Extension
14 Upper Protrusion
15 Lower Protrusion
100 Pressure Measurement Device

The invention claimed is:

1. A probe for measuring a lip closing force, the probe comprising:
   a hollow balloon configured to be disposed between upper and lower lips of a subject, and crushed and deformed by the lip closing force; and
   a base which communicates with the inside of the balloon, and is connected to a pressure measurement device for measuring an internal pressure of the balloon, wherein
   the balloon is provided with a fixable portion that has the shape of a plate and that is configured to be sandwiched between teeth or gums of the subject, wherein the fixable portion is disposed at a medial portion of the balloon with respect to a vertical direction that is normal to a direction of insertion of the balloon when inserted between the lips.

2. The probe of claim 1, wherein
   the fixable portion has the shape of a plate configured to extend from the medial portion of the balloon in a direction of insertion of the balloon when inserted between the lips.

3. The probe of claim 1, wherein
   the fixable portion is configured to extend to a position corresponding to front teeth in an oral cavity of the subject such that the fixable portion is configured to be sandwiched between the front teeth or gums of the subject.

4. The probe of claim 3, wherein
   the fixable portion is provided with a protrusion protruding in a vertical direction.

5. The probe of claim 1, wherein
   the fixable portion is configured to extend to a position corresponding to back teeth in an oral cavity of the subject such that the fixable portion is configured to be sandwiched between the back teeth or gums of the subject.

6. The probe of claim 5, wherein
   the fixable portion includes a right extension configured to extend rightward with respect to the oral cavity of the subject, and a left extension configured to extend leftward in the oral cavity of the subject.

7. The probe of claim 1, wherein
   the fixable portion is integrally molded with the balloon.

* * * * *